(12) United States Patent
Hiltner

(10) Patent No.: US 6,485,445 B1
(45) Date of Patent: Nov. 26, 2002

(54) CONVERTIBLE ARM SUPPORTING APPARATUS

(76) Inventor: Debra A. Hiltner, 901 E. 13$^{th}$ St., Yankton, SD (US) 57078

( * ) Notice: Subject to any disclaimer, the term of this patent is extended or adjusted under 35 U.S.C. 154(b) by 11 days.

(21) Appl. No.: 09/853,479

(22) Filed: May 11, 2001

(51) Int. Cl.$^7$ .................................................. A61F 5/00
(52) U.S. Cl. ............................ 602/4; 602/20; 128/845
(58) Field of Search ........................... 602/4, 5, 20, 26, 602/61, 62, 64, 65; 128/877, 878, 879, 881, 882, 845

(56) References Cited

U.S. PATENT DOCUMENTS

| | | | |
|---|---|---|---|
| 1,808,422 A | * | 6/1931 | MacDonald ................. 602/4 |
| 2,460,589 A | * | 2/1949 | Lewis |
| 4,564,008 A | * | 1/1986 | Donahoo |
| 4,834,082 A | * | 5/1989 | Ghadiali |
| 4,896,660 A | * | 1/1990 | Scott |
| 4,986,266 A | * | 1/1991 | Lindemann |
| 5,413,552 A | * | 5/1995 | Iwuala |
| D365,636 S | * | 12/1995 | Kilbey |
| 5,651,143 A | * | 7/1997 | Zehrung |
| 6,030,354 A | * | 2/2000 | Lakusiewicz |
| 6,099,489 A | * | 8/2000 | Herzberg .................. 602/4 |
| 6,110,133 A | * | 8/2000 | Ritts |

* cited by examiner

Primary Examiner—Michael A. Brown

(57) ABSTRACT

A convertible arm supporting apparatus for providing supplemental support for facilitating immobilization of an injured arm includes an elongate suspending member for extending over a shoulder of a user. The suspending member includes a first end portion, a second end portion, and an intermediate portion between the first and second end portions. The suspending member also includes connections located on each of the first and second end portions for removably connecting a distal end of the end portion to a location on the end portion toward the intermediate portion to form a loop for receiving a portion of the forearm of the user. The intermediate portion has an aperture therein forming laterally spaced sections of the intermediate portion on lateral sides of the aperture, and the laterally spaced sections are formed of a flexible material such that the sections are adaptable to contours on opposite sides of the shoulder of the user to form a pocket for embracing a portion of the user's shoulder. Optionally, an arm receiving member defines a channel for positioning a forearm of the user therein, and is adapted for removably mounting the arm receiving member to the first end portion and the second end portion of the suspending member.

19 Claims, 4 Drawing Sheets

CONVERTIBLE ARM SUPPORTING APPARATUS

BACKGROUND OF THE INVENTION

1 Field of the Invention

The present invention relates to arm supports and more particularly pertains to a new convertible arm supporting apparatus for providing supplemental support for facilitating immobilization of an injured arm.

2 Description of the Prior Art

The use of arm supports is known in the prior art. Some of the known arm supports support the arm at two or more discrete locations along the user's forearm. This type of support tends to be less bulky and heavy, which some patients tend to favor. However, this type of support may also cause uncomfortable pressure points on the arm of the user as a result to the weight of the arm resting on the support at only two locations. Another type of support provides substantially continuous support along the length of the user's forearm, which tends to avoid any points of high pressure on the forearm. However, this type of support tends to be bulky and can be heavy, which places greater stress on the part of the body (such as, for example, the shoulder) supporting the arm support. While some persons may favor one of these types of supports, other persons may favor the other type of support. In order to satisfy both preferences, a rehabilitation facility must have both types of supports on hand if persons with both types of preferences are to be satisfied. This can lead to additional costs for the rehabilitation facility, and make the rehabilitative process more costly to the patient and the insurance company.

The convertible arm supporting apparatus according to the present invention substantially departs from the conventional concepts and designs of the prior art, and in so doing provides an apparatus primarily developed for the purpose of providing supplemental support for facilitating immobilization of an injured arm.

SUMMARY OF THE INVENTION

In view of the foregoing disadvantages inherent in the known types of arm supports now present in the prior art, the present invention provides a new convertible arm supporting apparatus construction wherein the same can be utilized for providing supplemental support for facilitating immobilization of an injured arm.

To attain this, the present invention generally comprises an elongate suspending member for extending over a shoulder of a user. The suspending member includes a first end portion, a second end portion, and an intermediate portion between the first and second end portions. The suspending member also includes connections located on each of the first and second end portions for removably connecting a distal end of the end portion to a location on the end portion toward the intermediate portion to form a loop for receiving a portion of the forearm of the user. The intermediate portion has an aperture therein forming laterally spaced sections of the intermediate portion on lateral sides of the aperture, and the laterally spaced sections are formed of a flexible material such that the sections are adaptable to contours on opposite sides of the shoulder of the user to form a pocket for embracing a portion of the user's shoulder. Optionally, an arm receiving member is provided for cradling a portion of the user's arm. The arm receiving member defines a channel for positioning a forearm of the user therein, and is adapted for removably mounting the arm receiving member to the first end portion and the second end portion of the suspending member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a schematic sectional view of the intermediate portion of the suspending member in relation to the shoulder of the user.

DESCRIPTION OF THE PREFERRED EMBODIMENT

Figure 1:
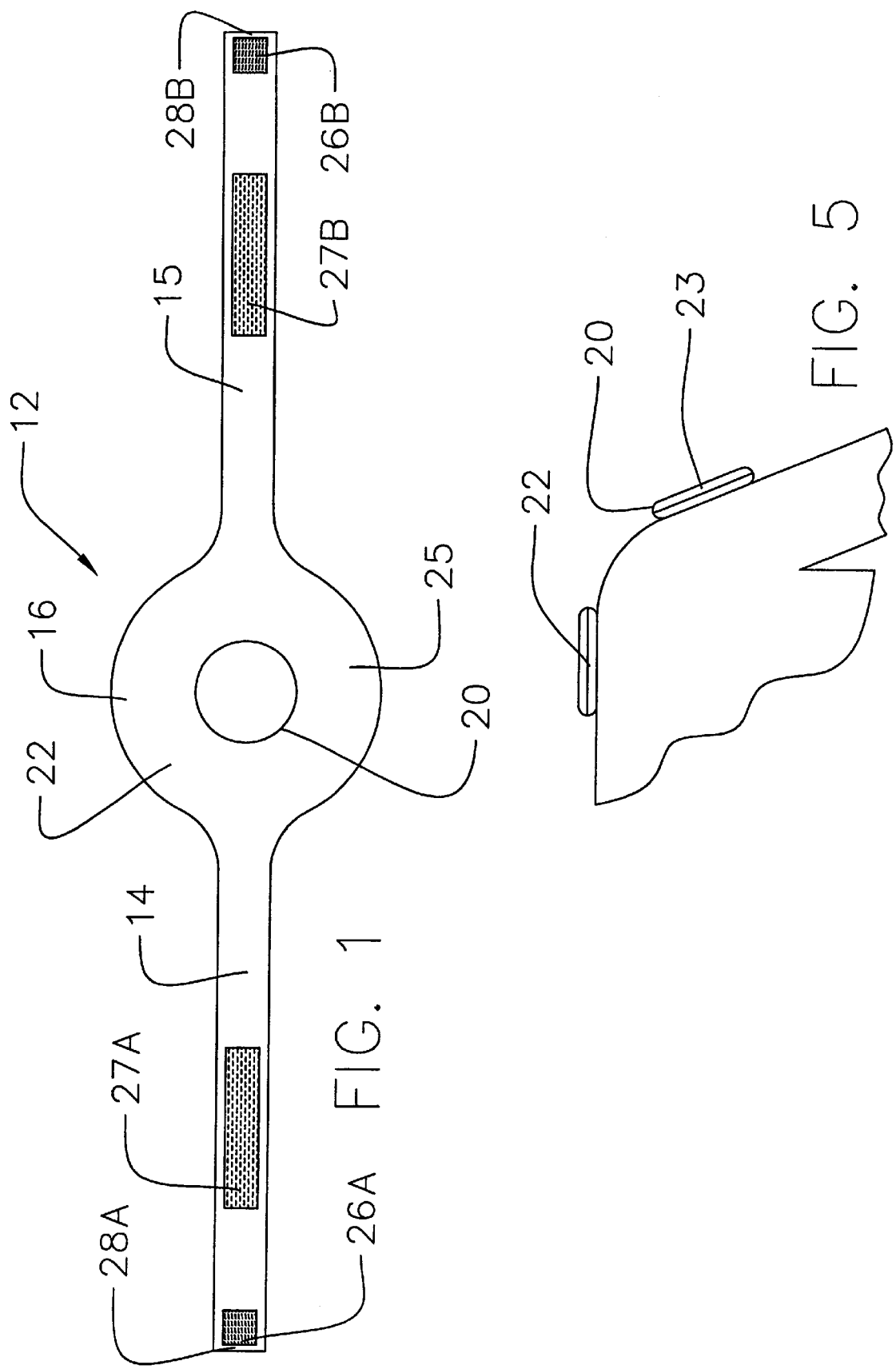
FIG. 1 is a schematic top view of the suspending member of a new convertible arm supporting apparatus according to the present invention.
Figure 2:
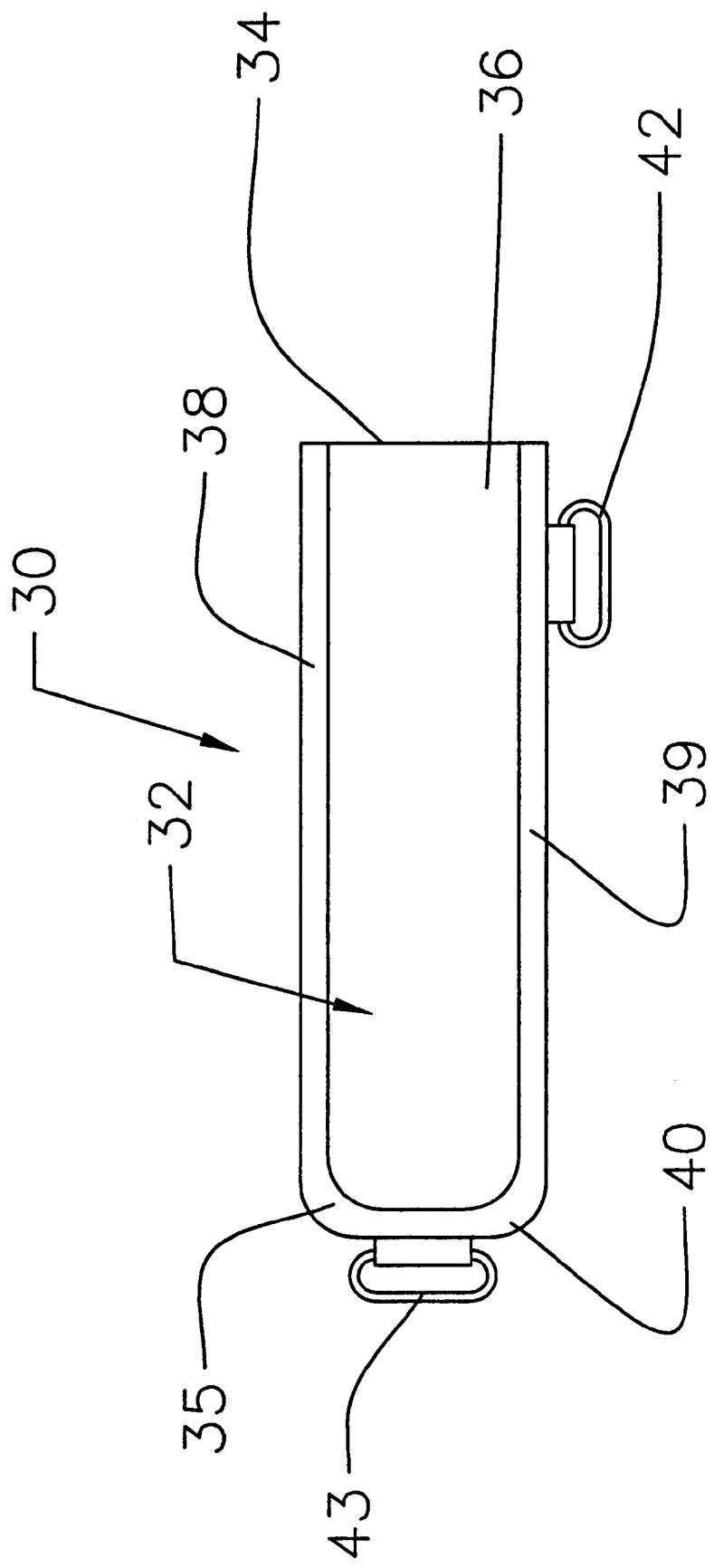
FIG. 2 is a schematic top view of the arm receiving member of the present invention.
Figure 3:
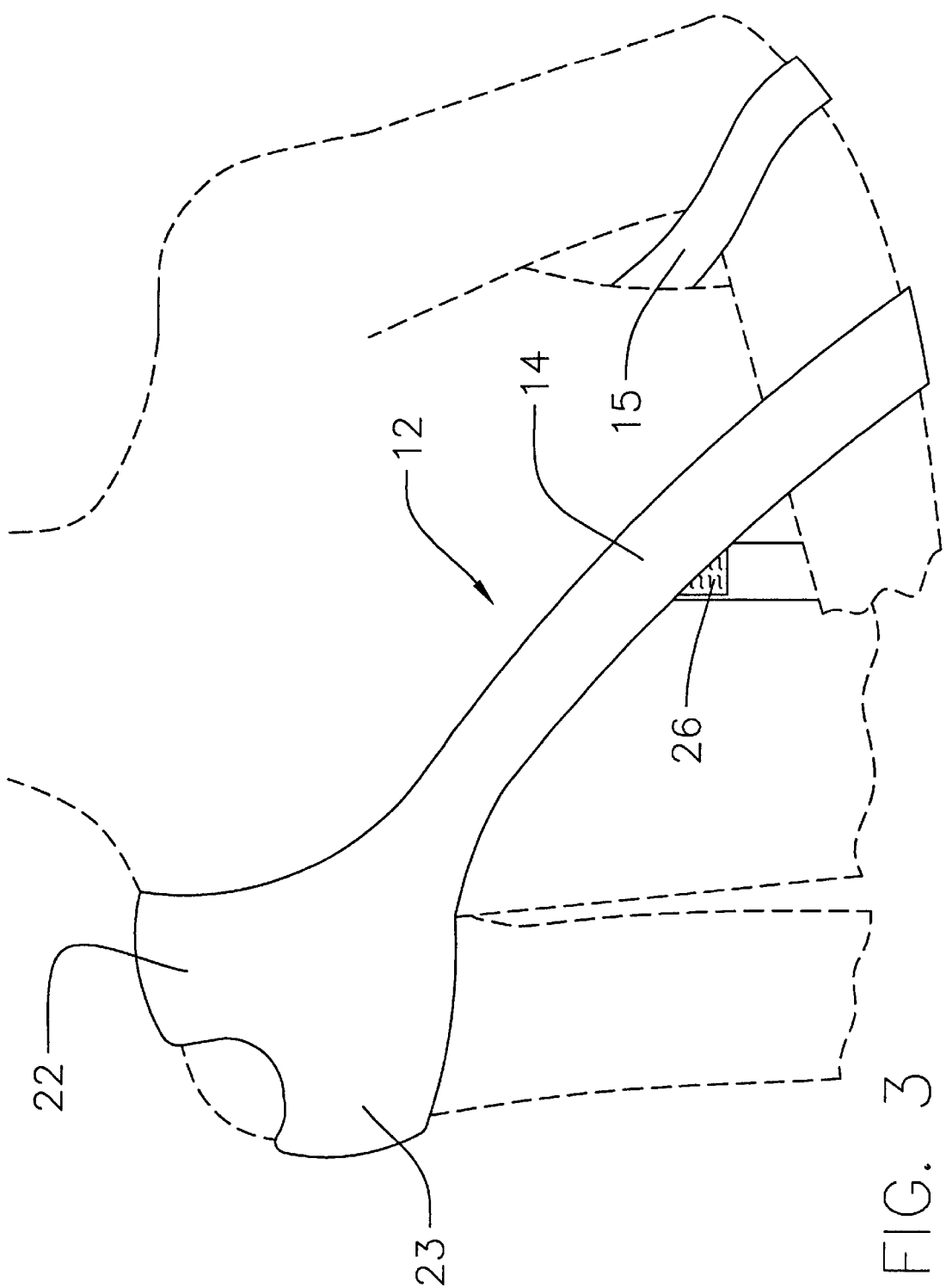
FIG. 3 is a schematic front view of the suspending member of the present invention positioned on a user's body.
Figure 4:
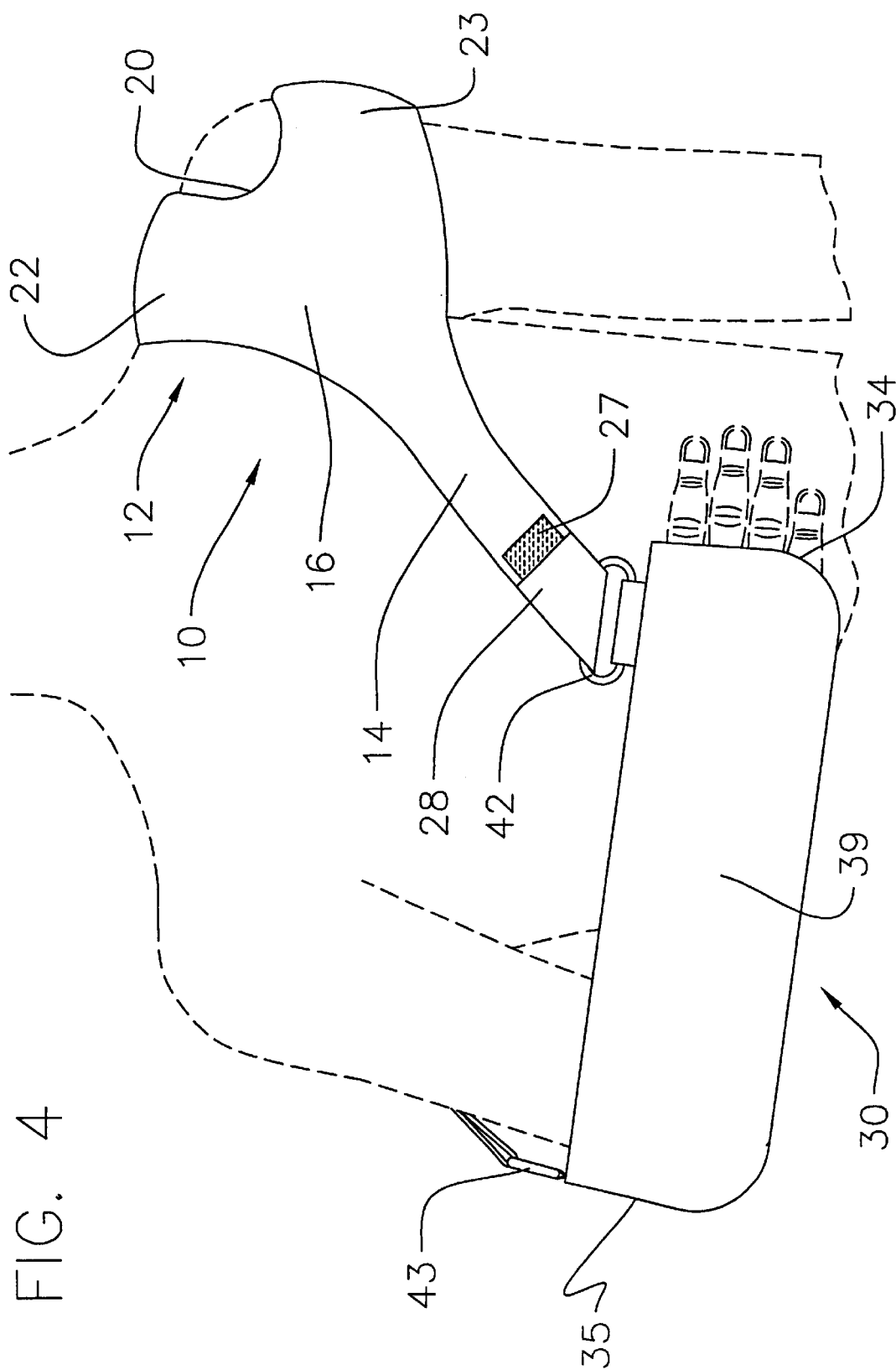
FIG. 4 is a schematic front view of the suspending member and arm receiving member of the present invention positioned on a user's body.

With reference now to the drawings, and in particular to FIGS. 1 through 5 thereof, a new convertible arm supporting apparatus embodying the principles and concepts of the present invention and generally designated by the reference numeral 10 will be described.

As best illustrated in FIGS. 1 through 5, the convertible arm supporting apparatus 10 generally comprises a suspending member 12 and, optionally, an arm receiving member 30 that is removably mountable on the suspending member.

The suspending member 12 of the invention is provided for extending over a shoulder of a user, and is generally elongate. The suspending member 12 comprises a first end portion 14, a second end portion 15, and an intermediate portion 16 located between the first and second end portions. In the illustrative embodiment of the invention, the width of the intermediate portion is greater than the width of the first 14 and second 15 end portions. The width of the intermediate portion may be approximately three to five times the width of the first and second end portions. Also, in the illustrative embodiment, the first and second end portions each have a substantially uniform width along their respective lengths, and the first and second end portions have substantially equal widths. One of the end portions may have a length that is somewhat longer than a length of the other of the end portions to accommodate a somewhat longer distance that must be traversed by the end portion positioned against the back of the user as compared to the distance traversed by the end portion positioned against the front of the user.

One significant aspect of the invention is an aperture 20 in the intermediate portion 16 of the suspending member. The aperture 20 forms a pair of laterally spaced sections 22, 23 of the intermediate portion on lateral sides of the aperture. The laterally spaced sections 22, 23 are preferably formed of a flexible material such that the sections are adaptable to contours on opposite sides of the shoulder of the user to form a pocket for embracing a portion of the user's shoulder. The aperture permits greater bending or flexing of the sections with respect to each other than if the intermediate portion was continuous across the width of the intermediate portion. One of the sections 22 is thus adapted for resting against an upper or top surface of the user's shoulder while the other of the sections 23 is adapted for resting against a side surface of the shoulder, with the protrusion of the shoulder partially extending into the aperture of the intermediate portion. The weight of the user's supported forearm tends to pull the intermediate portion over the user's shoulder and nest a portion of the shoulder in the aperture. The aperture 20 may be located substantially centrally in the intermediate portion. Optionally, the intermediate portion may have a lower surface that is padded with a relatively softer material (see FIG. 5).

Connecting means are located on each of the first and second end portions for removably connecting a distal end of the end portion to a location on the end portion toward the intermediate portion. In the illustrative embodiment, the connecting means comprises two components on each of the end portions 14, 15. A first component 26A, 26B is mounted on the distal end 28A, 28B of the end portion, and a second component 27A, 27B is mounted on the end portion between the first component and the intermediate portion. The first 26A, 26B and second 27A, 27B components are removably connectable to each other to form a loop for receiving a portion of the forearm of the user in the loop. The size of the loop is thus adjustable for securing about the forearm of the user and holding the loop in place on the forearm. The second component 27A, 27B extends along a portion of a length of the end portion. Each of the end portions has a length, and the second component 27A, 27B may extend along approximately one-third of the length of the end portion to permit adjustment of the size of the loop formed by the end portion. Each of the end portions has opposite sides, and the first and second components may be mounted on a same one of the opposite sides of the end portions. In the illustrative embodiment, the first 26A, 26B and second 27A, 27B components comprise a pair of complementary hook and loop fasteners, although other fastening structures may also be used.

The end portions of the suspending member are thus adapted for securing directly to the arm of the user for supporting the arm adjacent to the body of the user. Optionally, the invention includes the arm receiving member 30 for cradling a portion of the user's arm. The arm receiving member 30 is removably mountable on the first and second end portions of the suspending member. The arm receiving member 30 defines a channel 32 for positioning the forearm of the user therein. The arm receiving member 30 has a first end 34 and a second end 35. The channel 32 of the arm receiving member 30 is substantially open at the first end 34 and is substantially closed at the second end 35. The arm receiving member may comprise a base wall 36 and side walls 38, 39. The side walls 38, 39 extend from the base wall 36. The side walls may extend generally perpendicular with respect to the base wall. An end wall 40 may extend from the base wall 36 at the second end 35 of the arm receiving member to close the second end.

A first mounting means may be provided for removably mounting the first end portion 14 of the suspending member 12 to the arm receiving member, and a second mounting means may be provided for removably mounting the second end portion 15 of the suspending member to the arm receiving member. The first mounting means is mounted on the arm receiving member adjacent to the first end 34 thereof and the second mounting means is mounted on the arm receiving member adjacent to the second end 35 thereof. In the illustrative embodiment, the first and second mounting means each comprise a loop 42, 43 mounted on the arm receiving member for receiving a portion of the end portion of the suspending member. The first 26A, 26B and second 27A, 27B components are connected to form loops on the end portions that extend through the respective loops 42, 43 and the position of the arm receiving member relative to the user's body may be adjusted by adjusting the size of the loop of the end portion.

In use, the intermediate portion of the suspending member is positioned with one of the sections of the intermediate member resting on the top of the shoulder of the user, and the other of the sections of the intermediate portion resting against the side of the shoulder and upper arm area of the user. The shoulder on which the intermediate portion is mounted is opposite of the arm having the forearm that needs support. Optionally, the end portions of the suspending member may be formed into a loop using the connecting components 26A, 26B, 27A, and 27B on each end portion, and the loop of one end portion is positioned toward the elbow of the forearm of the user and the other end portion is positioned toward the wrist of the firearm of the user. Alternatively, the invention is easily converted to use the arm receiving member with the suspending member by looping each of the end portions through one of the loops on the arm receiving member so that the suspending member supports the arm receiving member.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An arm support apparatus comprising:
   a suspending member for extending over a shoulder of a user, the suspending member being elongate, the suspending member comprising:
      a first end portion, a second end portion, and an intermediate portion between the first and second end portions;
      connecting means located on each of the first and second end portions for removably connecting a distal end of the end portion to a location on the end portion toward the intermediate portion to form a loop for receiving a portion of the forearm of the user; and
   wherein the intermediate portion has an aperture therein forming laterally spaced sections of the intermediate portion on lateral sides of the aperture, the laterally spaced sections being formed of a flexible material such that the sections are adaptable to contours on opposite sides of the shoulder of the user to form a pocket for embracing a portion of the user's shoulder;
   wherein each of the connecting means comprises two components, a first component of the connecting means being mounted on the distal end of the end portion, a second component of the connecting means being mounted on the end portion between the first component and the intermediate portion.

2. The arm support apparatus of claim 1 additionally comprising an arm receiving member for cradling a portion of the user's arm, the arm receiving member defining a channel for positioning a forearm of the user therein, the arm receiving member having a first end and a second end.

3. The arm support apparatus of claim 2 wherein the channel of the arm receiving member is substantially open at the first end and substantially closed at the second end, the arm receiving member comprising a base wall and side walls, the side walls extending from the base wall, the side walls extending generally perpendicular to the base wall, an end wall extending from the base wall at the second end of the arm receiving member.

4. The arm support apparatus of claim 2 wherein the arm receiving member includes a first mounting means for removably mounting the first end portion of the suspending member and a second mounting means for re movably mounting the second end portion of the suspending member.

5. The arm support apparatus of claim 4 wherein the first mounting means is mounted on the arm receiving member adjacent to the first end thereof and the second mounting means is mounted on the arm receiving member adjacent to the second end thereof.

6. The arm support apparatus of claim 4 wherein the first and second mounting means each comprise a loop mounted on the arm receiving member for receiving a portion of the end portion of the suspending member.

7. The arm support apparatus of claim 1 wherein the second component extends along a portion of a length of the end portion, wherein each of the end portions having a length, the second component extending along approximately one-third of the length of the end portion.

8. The arm support apparatus of claim 1 wherein the end portions each have opposite sides, the first and second components being mounted on a same one of the opposite sides of the end portions.

9. The arm support apparatus of claim 1 wherein a width of the intermediate portion of the suspending member is greater than a width of the first and second end portions.

10. The arm support apparatus of claim 9 wherein the width of the intermediate portion being approximately three to five times the width of the first and second end portions.

11. The arm support apparatus of claim 1 wherein the first and second end portions each have a substantially uniform width, and the first and second end portions have substantially equal widths.

12. The arm support apparatus of claim 1 wherein each of said end portions have a length, and wherein the length of one of the end portions is greater than the length of the other of the end portions.

13. The arm support apparatus of claim 1 wherein the aperture is substantially centrally-located on the intermediate portion.

14. An arm support apparatus comprising:
   a suspending member for extending over a shoulder of a user, the suspending member being elongate, the suspending member comprising:
      a first end portion, a second end portion, and an intermediate portion between the first and second end portions;
      the intermediate portion having an aperture therein forming laterally spaced sections of the intermediate portion on lateral sides of the aperture, the laterally spaced sections being formed of a flexible material such that the sections are adaptable to contours on opposite sides of the shoulder of the user to form a pocket for embracing a portion of the user's shoulder, the aperture being substantially centrally-located on the intermediate portion;
      connecting means located on each of the first and second end portions for removably connecting a distal end of the end portion to a location on the end portion toward the intermediate portion;
         wherein each of the connecting means comprises two components, a first component of the connecting means being mounted on the distal end of the end portion, a second component of the connecting means being mounted on the end portion between the first component and the intermediate portion;
         wherein the second component extends along a portion of a length of the end portion, wherein each of the end portions having a length, the second component extending along approximately one-third of the length of the end portion;
         wherein the end portions each have opposite sides, the first and second components being mounted on a same one of the opposite sides of the end portions;
      wherein a width of the intermediate portion being greater than a width of the first and second end portions, the width of the intermediate portion being approximately three to five times the width of the first and second end portions;
      wherein the first and second end portions each have a substantially uniform width, the first and second end portions having substantially equal widths;
   an arm receiving member for cradling a portion of the user's arm, the arm receiving member defining a channel for positioning a forearm of the user therein, the arm receiving member having a first end and a second end, the arm receiving member including a first mounting means for removably mounting the first end portion of the suspending member and a second mounting means for removably mounting the second end portion of the suspending member;

wherein the channel of the arm receiving member is substantially open at the first end and substantially closed at the second end, the arm receiving member comprising a base wall and side walls, the side walls extending from the base wall, the side walls extending generally perpendicular to the base wall an end wall extending from the base wall at the second end of the arm receiving member;

wherein the first mounting means is mounted on the arm receiving member adjacent to the first end thereof and the second mounting means is mounted on the arm receiving member adjacent to the second end thereof;

wherein the first and second mounting means each comprise a loop mounted on the arm receiving member for receiving a portion of the end portion of the suspending member.

15. An arm support apparatus comprising:

an elongate suspending member for extending over a shoulder of a user, the suspending member comprising:

a first end portion, a second end portion, and an intermediate portion between the first and second end portions;

connecting means located on each of the first and second end portions for removably connecting a distal end of the end portion to a location on the end portion toward the intermediate portion to form a loop for receiving a portion of the forearm of the user; and wherein the intermediate portion has an aperture therein forming laterally spaced sections of the intermediate portion on lateral sides of the aperture, the laterally spaced sections being formed of a flexible material such that the sections are adaptable to contours on opposite sides of the shoulder of the user to form a pocket for embracing a portion of the user's shoulder;

an arm receiving member for cradling a portion of the user's arm, the arm receiving member defining a channel for positioning a forearm of the user therein, the arm receiving member having a first end and a second end;

wherein the arm receiving member includes a first mounting means for removably mounting the first end portion of the suspending member and a second mounting means for removably mounting the second end portion of the suspending member; and wherein the first and second mounting means each comprise a loop mounted on the arm receiving member for receiving a portion of the end portion of the suspending member.

16. The arm support apparatus of claim 15 wherein the second component extends along a portion of a length of the end portion, wherein each of the end portions having a length, the second component extending along approximately one-third of the length of the end portion.

17. The arm support apparatus of claim 15 wherein the end portions each have opposite sides, the first and second components being mounted on a same one of the opposite sides of the end portions.

18. The arm support apparatus of claim 15 wherein the channel of the arm receiving member is substantially open at the first end and substantially closed at the second end, the arm receiving member comprising a base wall and side walls, the side walls extending from the base wall, the side walls extending generally perpendicular to the base wall, an end wall extending from the base wall at the second end of the arm receiving member.

19. The arm support apparatus of claim 15 wherein the first mounting means is mounted on the arm receiving member adjacent to the first end thereof and the second mounting means is mounted on the arm receiving member adjacent to the second end thereof.

\* \* \* \* \*